United States Patent [19]

Gauthier et al.

[11] 4,108,997
[45] Aug. 22, 1978

[54] DIURETIC [2]BENZOPYRANO[4,3-B]PYRIDINES AND PROCESS THEREFOR

[75] Inventors: Jean A. Gauthier, Montreal; Leslie G. Humber, Dollard des Ormeaux; Clara Revesz, Montreal, all of Canada

[73] Assignee: Ayerst, McKenna & Harrison Limited, Montreal, Canada

[21] Appl. No.: 752,655

[22] Filed: Dec. 20, 1976

[51] Int. Cl.² .................. A61K 31/445; C07D 491/04
[52] U.S. Cl. .............................. 424/256; 260/293.55; 260/293.83; 260/297 R; 260/347.8
[58] Field of Search .................... 260/293.55; 424/256

[56] References Cited

U.S. PATENT DOCUMENTS

| | | | |
|---|---|---|---|
| 3,514,464 | 5/1970 | Pars et al. | 260/293.55 |
| 3,946,008 | 3/1976 | Brown et al. | 424/246 |

*Primary Examiner*—Henry R. Jiles
*Assistant Examiner*—Richard A. Schwartz
*Attorney, Agent, or Firm*—Stephen Venetianer

[57] ABSTRACT

[2]Benzopyrano[4,3-b]pyridine derivatives characterized by having a 2,3,4,4a,6,10b-hexahydro-1H-[2]benzopyrano[4,3-b]pyridine nucleus bearing substituents at positions 1,6,8 and 9 are disclosed. The derivatives are useful diuretic agents. Methods for their preparation and use also are disclosed.

10 Claims, No Drawings

DIURETIC [2]BENZOPYRANO[4,3-B]PYRIDINES AND PROCESS THEREFOR

BACKGROUND OF THE INVENTION

1. Field of the Invention

This invention relates to novel [2]benzopyrano[4,3-b]pyridine derivatives, to processes for their preparation, to methods for using the derivatives and to pharmaceutically acceptable compositions of said derivatives.

More specifically, the present invention relates to novel 2,3,4,4a,6,10b-hexahydro-1H-[2]benzopyrano[4,3-b]pyridine derivatives possessing valuable pharmacologic properties. For example, these derivatives are useful diuretic agents at dosages which do not elicit undesirable side effects. The combination of this pharmacologic property with a low order of toxicity render the [2]benzopyrano[4,3-b]pyridine derivatives of the invention therapeutically useful.

2. Description of the Prior Art

A number of prior art reports dealing with benzopyranopyridines are available. For example, the [1]benzopyrano[3,4-c]pyridine ring system is described in the German Pat. No. 2,263,100, issued July 12, 1973 and by H. G. Pars and F. E. Granchelli in the U.S. Pat. No. 3,535,327, issued Oct. 20, 1970 and U.S. Pat. No. 3,632,595, issued Jan. 4, 1972. In addition, the fully unsaturated [2]benzopyrano[4,3-b]pyridin-6-one ring system is described by N. Dennis et al., J. Chem. soc., Perkin Trans. 1, 750(1974). The [2]benzopyrano[4,3-b]pyridine derivatives of the present invention are distinguished from the prior art compounds by having a fully saturated pyridine ring and by the nature of the substituents on the ring system. Furthermore, the compounds of the present invention are distinguished from the prior art compounds by their unique pharmacological properties.

SUMMARY OF THE INVENTION

The compounds of this invention are represented by formula I

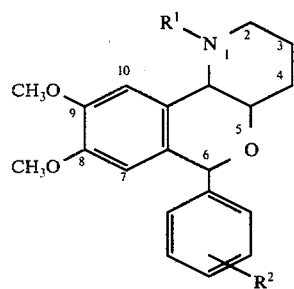

in which $R^1$ is lower alkyl or lower cycloalkyl(lower)alkyl and $R^2$ is hydrogen or halo.

Also included are the therapeutically acceptable acid addition salts of the compounds of formula I.

The novel [2]benzopyrano[4,3-b]pyridine derivatives of formula I are prepared by condensing a compound of formula II

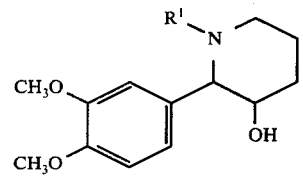

in which $R^1$ is as defined herein with an aldehyde of formula III

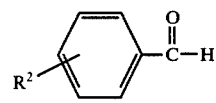

in which $R^2$ is as defined herein in the presence of an acid catalyst to obtain the corresponding compound of formula I in which $R^1$ and $R^2$ are as defined herein.

Another aspect of this invention involves a method for increasing the excretion of urine (diuresis) in a mammal which comprises administering to said mammal an effective diuretic amount of a compound of formula I, or a therapeutically acceptable salt thereof.

Still another aspect of this invention involves a pharmaceutical composition comprising a compound of formula I, or a therapeutically acceptable salt thereof, and a pharmaceutically acceptable carrier.

DETAILED DESCRIPTION OF THE INVENTION

The term "lower alkyl" as used herein contemplates straight chain alkyl radicals containing from one to six carbon atoms and branched chain alkyl radicals containing from three to four carbon atoms and includes methyl, ethyl, propyl, isopropyl, butyl, isobutyl, pentyl, hexyl and the like.

The term "lower cycloalkyl" as used herein contemplates saturated cyclic hydrocarbon radicals containing from three to six carbon atoms and includes cyclopropyl, cyclobutyl, cyclohexyl and the like.

The term "lower alkanoyl" as used herein contemplates straight chain alkanoyl radicals containing from two to six carbon atoms and a branched chain alkanoyl radical containing four carbon radicals and includes acetyl, propionyl, isobutyryl, hexanoyl and the like.

The term "lower cycloalkyl(lower)alkyl" as used herein contemplates a lower cycloalkyl(lower)alkyl radical in which the alkyl portion thereof is a straight chain containing from one to six carbon atoms or a branched chain containing from two to four carbon atoms and includes cyclopropylmethyl, 5-cyclobutylpentyl, 1-methyl-3-cyclopentylpropyl, 2-ethyl-2-cyclohexylethyl and the like. Thus, the lower cycloalkyl(lower)alkyl can contain 4 to 12 carbon atoms.

The term "halo" as used herein contemplates halogens and includes fluorine, chlorine, bromine and iodine, unless stated otherwise.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, ether (i.e., diethyl ether) or an ethanol-ether mixture. These salts, when administered to a mammal, possess the same pharmacologic activities as the corresponding bases. For many purposes it is preferable to administer the salts rather than the base compounds. Suitable acids to form these salts include, for example the common mineral acids, hydrohalic, sulfuric or phosphoric, as well as the organic acids, formic, acetic, maleic, citric, or tartaric acid, or acids which are sparingly soluble in body fluids and which impart slow-release properties to their respective salts such as pamoic or tannic acid or carboxymethyl cellulose. The addition salts thus obtained are the functional eqivalent of the parent base compound in respect to their therapeutic use. Hence, these addition salts are included within the scope of this invention and are limited only by the requirement that the acids employed in forming the salts be therapeutically acceptable.

Also included in this invention are the stereochemical isomers of the compounds of formula I which result from asymmetric centers, contained therein.

Individual optical isomers, which might be separated by fractional crystallization of the diastereoisomeric salts thereof, for instance, salts with d- or l-tartaric acid or D-(+)-α-bromocamphor sulfonic acid, are also included.

The compounds of this invention of formula I or a therapeutically acceptable salt thereof are useful diuretic agents in a mammal upon oral or parenteral administration.

The compounds of formula I are shown to be effective diuretic agents in mammals by tests conducted in dogs or rats. An example of such a test for diuretic agents in rats is described by J. R. Cummings et al., J. Pharmacol. Exp. Ther., 414, 128(1960). In this test, the urine of the rats is collected for 5 hours, during which time food and water are withdrawn. Urine volumes as well as sodium, potassium and chloride ion concentrations are determined. The compounds of this invention exhibit a dose response dependency when they are orally administered in dosages ranging from 5 to 150 mg per kilogram of body weight. The following representative compounds of this invention are effective diuretic agents in the dog or rat at oral dosages ranging from 5 to 25 mg per kilogram of body weight: [4aα,10bα]-2,3,4,4a,6,10b-hexahydro-1-ethyl-8,9-dimethoxy-6-phenyl-1H-[2]benzopyrano[4,3-b]pyridine (Example 7) and [4aα,10bα]-2,3,4,4a,6,10b-hexahydro-1-cyclopropylmethyl-8,9-dimethoxy-6-phenyl-1H-[2]benzopyrano[4,3-b]pyridine (Example 7).

When the compounds of formula I of this invention are used as diuretic agents in mammals, e.g., rats and dogs, they are used alone or in combination with pharmacologically acceptable carriers, the proportion of which is determined by the solubility and chemical nature of the compound, chosen route of administration and standard biological practice. For example, they are administered orally in solid form i.e., capsule or tablet. They are also administered orally in the form of suspensions or solutions or they may be injected parenterally. For parenteral administration they may be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of the invention contain the active ingredient in admixture with one or more non-toxic pharmaceutical excipients known to be suitable in the manufacture of aqueous suspensions. Suitable excipients are, for example, methyl-cellulose, sodium alginate, gum acacia, lecithin and so forth. The aqueous suspensions can also contain one or more preservatives, one or more colouring agents and/or one or more sweetening agents.

Non-aqueous suspensions can be formulated by suspending the active ingredient in a vegetable oil, for example, arachic oil, olive oil, sesame oil, or coconut oil; or in a mineral oil, for example liquid paraffin. The suspension can contain a thickening agent, for example beeswax, hard paraffin or cetyl alcohol. These compositions can also contain a sweetening agent, flavouring agent and antioxidant.

The dosage of the compounds of formula I of this invention as diuretic agents will vary with the form of administration and the particular host as well as the age and condition of the host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. The effective diuretic amount of the compounds usually ranges from about 1.0 mg to about 500 mg per kilogram of body weight per day, although as aforementioned variations will occur. However a dosage level that is in range of from about 10 mg to about 300 mg per kilogram of body weight per day is employed most desirably in order to achieve effective results.

PROCESSES

The novel [2]benzopyrano[4,3-b]pyridine derivatives of this invention are readily and conveniently prepared by the following process:

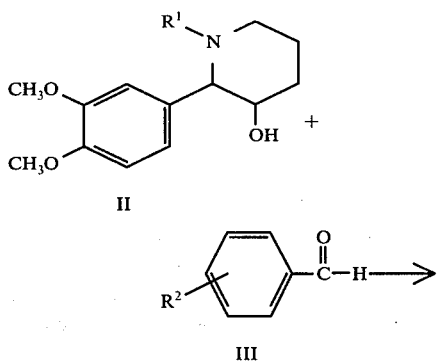

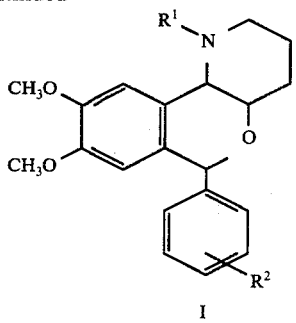

in which R¹ and R² are as defined herein.

The compounds of formula I can exist as two isomers depending upon which isomer of formula II is used as starting material. These compound I isomers are designated cis or trans isomer, reference being given to the hydrogen atoms at positions 4a and 10b. In a preferred embodiment, the cis isomer of formula IIa gives the cis isomer of formula Ia, as illustrated by the following scheme.

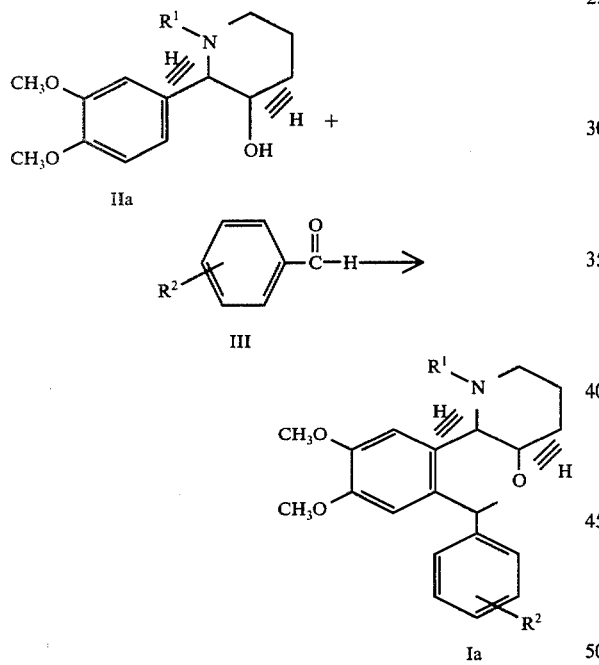

in which R¹ and R² are as defined herein.

With reference to the above process the compound of formula II is condensed with one to five molar equivalents of the aldehyde of formula III in the presence of an acid catalyst to obtain the corresponding compound of formula I.

In practising the condensation (II + III → I) any solvent inert to the reaction conditions can be used. Suitable solvents include the cyclic ethers (i.e., dioxane, tetrahydrofuran and the like). Dioxane is especially convenient and practical for this use. The preferred acid catalysts for this condensation can be selected from anhydrous hydrogen chloride, hydrogen bromide or boron trifluoride etherate. The amount of acid catalyst is not especially critical and may range from 5 to 100 molar equivalents. The time of the reaction can range from 0.5 to 60 hours, with the preferred range from 1 to 24 hours, and the temperature can range from −20° to 100° C or the boiling point of the reaction mixture; preferable temperatures are from 0° to 50° C. During the reaction it is advantageous to remove the water formed from the condensation. The addition of an anhydrous alkali-aluminum silicate (molecular sieves) to the reaction mixture is an effective means to remove the water.

Useful and practical starting materials for the preparation of the compound of formula I are the 1-substituted-2-(3,4-dimethoxyphenyl)-3-piperidinols of formula II.

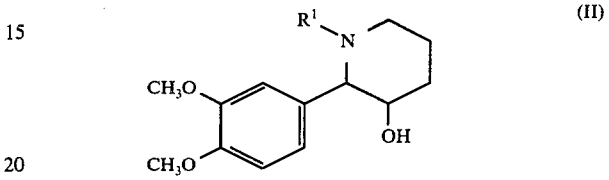

in which R¹ is as defined herein.

The starting materials of formula IIa for the preferred embodiment are readily prepared by the following process.

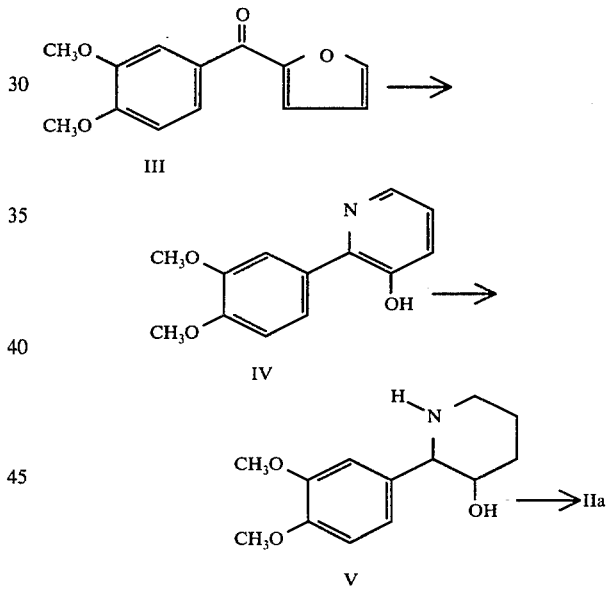

With reference to this process, 3,4-dimethoxybenzonitrile is reacted with furyllithium at low temperature according to the process described A. P. Dunlop and S. Swadesh, U.S. Pat. No. 2,636,882, issued Apr. 28, 1953 to obtain 2-(3,4-dimethoxybenzolyl)furan of formula III. The latter compound is heated in a solution of ammonium hydroxide in methanol, in the manner described by A. P. Dunlop and S. Swadesh, U.S. Pat. No. 2,672,461, issued Mar. 16, 1954 to obtain 2-(3,4-dimethoxyphenyl)-3-pyridinol of formula IV. Reduction of the latter compound, preferably with hydrogen and Raney nickel according to the procedure of L. A. Walter et al., J. Med. Chem., II 792(1968), gives cis-2-(3,4-dimethoxyphenyl-3-piperidinol of formula V.

The compound of formula V is readily converted to the cis-1-substituted-2-(3,4-dimethoxyphenyl)-3-piperidinol of formula IIa. For instance, reaction of the compound of formula V with formaldehyde in ethanol in the presence of acetic acid, followed by hydrogenation in the presence of a noble metal catalyst (i.e., platinum oxide, "Adams catalyst") gives the compound of formula IIa in which $R^1$ is methyl. Another conversion comprises acylating the compound of formula V with a lower alkanoyl halide, lower cycloalkylcarboxyl halide or lower cycloalkyl(lower)alkanoyl halide, wherein the halide is chlorine, bromine or iodine, in an inert solvent (i.e., methylene chloride) in the presence of a inorganic proton acceptor (i.e., sodium or potassium hydroxide) to obtain the corresponding intermediate, a cis-1-acyl-2-(3,4-dimethoxyphenyl)-3-piperidinol. Reduction of the latter intermediate, preferably with lithium aluminum hydride in tetrahydrofuran at 0° to 30° C for 15 to 120 minutes, gives the corresponding compound of formula IIa in which $R^1$ is lower alkyl or lower cycloalkyl(lower)alkyl.

Alternatively, the compound of formula V is reacted with a lower alkyl halide or lower cycloalkyl(lower)alkyl halide wherein the halide is bromide, chloride or iodide in an inert solvent, such as methylene chloride, chloroform or the like, at a temperature from 40° C to the boiling point of the reaction mixture for about 20 to 40 hours to obtain the corresponding compound of formula IIa in which $R^1$ is as defined herein.

The following examples illustrate further this invention.

EXAMPLE 1

3,4-Dimethoxybenzonitrile 3,4-Dimethoxy-benzaldehyde (287 g, 1.73 moles) in ethanol (1 liter) is treated with a solution of hydroxylamine hydrochloride (147 g, 2.12 moles) in water (200 ml) followed by addition of 17N sodium hydroxide (150 ml). The reaction mixture is stirred overnight at room temperature, poured on ice, and solid carbon dioxide is added until the solution is neutral. Extraction with methylene chloride followed by drying and evaporation of the extracts gives an orange oil. Distilled acetic anhydride (410 g, 4.0 moles) is added dropwise to the oil. When the addition is complete, the mixture is heated at reflux for 0.5 hour, poured into water and stirred for 0.5 hour. The reaction mixture is extracted with diethyl ether and the organic extract is dried and evaporated to give an orange oil. The oil is distilled at 135°–140° C/0.5 mm and dissolved in methylene chloride. The solution is washed with 2N sodium hydroxide, dried and evaporated to give the title compound; nmr (CDCl$_3$) δ 3.94 (s, 6H) and 7.2 (m, 3H). EXAMPLE 2

2-(3,4-Dimethoxybenzoyl)furan; III

Freshly distilled furan (57 ml, 790 mmoles) in dry ether (500 ml) is cooled (5° C) under nitrogen and n-butyllithium (340 ml, 2.35M in hexane) is added dropwise to the stirred solution. The mixture is stirred for 3 days at room temperature. The mixture is cooled to −30° C and a solution of 3,4-dimethoxybenzonitrile (77.5 g, 480 mmoles, described in Example I) in ether (200 ml) is added dropwise to the mixture. The brown mixture is stirred for 5 hours at room temperature. Wet tetrahydrofuran is cautiously added and the mixture is poured on ice. Hydrochloric acid (3N) is added until the mixture is acidic. The mixture is extracted with ether. The aqueous phase is rendered basic and extracted with methylene chloride. The organic extract is washed with brine, dried and evaporated. The residue is subjected to chromatography on silica gel using chloroform and the eluates are evaporated to give the title compound, mp 112°–114° C.

EXAMPLE 3

2-(3,4-Dimethoxyphenyl)-3-pyridinol; IV 2-(3,4-Dimethoxybenzoyl)furan (764.0 g, 3.28 moles, described in Example 2) is heated at 140° C in an autoclave in the presence of concentrated ammonium hydroxide (7 liters) and methanol (6 liters) for 17 hours. The mixture is cooled and concentrated to 4 liters. Methylene chloride (3 liters) is added and the mixture is extracted with 8N aqueous sodium hydroxide (500 ml). The aqueous extract is washed with methylene chloride. Ice is added to the aqueous phase followed by 6N hydrochloric acid to bring the pH between 7.5–7.0. The brown precipitate is collected, dried and milled to give the title compound, mp 150°–155° C.

EXAMPLE 4 cis-2-(3,4-Dimethoxyphenyl)-3-piperidinol; V 2-(3,4-Dimethoxyphenyl)-3-pyridinol (10.0 g, 43.2 mmoles, described in Example 3) is dissolved in p-dioxane (60 ml) containing 0.1 ml of 12.5N sodium hydroxide. The solution is hydrogenated for 17 hours with Raney nickel catalyst (1.5 g) at 1750 p.s.i. and 140° C. The mixture is filtered and the filtrate is evaporated. The residue is subjected to chromatography on alumina (Woelm, basic activity I) using first chloroform as eluant and then a 1:10 methanol-chloroform solvent combination. The eluates are evaporated, dissolved in acetone and maleic acid is added. The precipitate is crystallized from isopropanol-hexane to give the title compound as the maleate salt, mp 180°–181° C.

EXAMPLE 5 cis-2-(3,4-Dimethoxyphenyl)-1-methyl-3-piperidinol; IIa ($R^1 = CH_3$)

A solution of cis-2-(3,4-dimethoxyphenyl)-3-piperidinol (19.0 g, 80 mmoles, described in Example 4), ethanol (200 ml), 37% aqueous formaldehyde (7.4 g, 91 mmoles) and glacial acetic acid (8.0 g, 131 mmoles) is stirred at room temperature for 2 hours. The solution is diluted to 300 ml with ethanol and hydrogenated in the presence of Adams catalyst (400 mg). The residue is subjected to chromatography on silica gel using chloroform, 5% methanol-chloroform and finally 20% methanol-chloroform. The appropriate eluates are evaporated and the residue is dissolved in acetone. Maleic acid is added, followed by ether. The precipitate is collected and crystallized from acetonitrile-ether to give the title compound as the maleate salt, mp 132°–134° C.

EXAMPLE 6 cis-2-(3,4-Dimethoxyphenyl)-1-ethyl-3-piperidinol; IIa ($R^1 = C_2H_5$)

Acetyl chloride (9.75 g, 125 mmoles) is added dropwise to a cooled (0° to 10° C) and stirred solution of cis-2-(3,4-dimethoxyphenyl)-3-piperidinol (25.0 g, 105 mmoles, described in Example 4) in methylene chloride (200 ml) and 8N sodium hydroxide (100 ml). The mixture is stirred for 30 minutes and the organic phase is separated. The aqueous phase is extracted with methylene chloride. The organic extracts are washed with dilute hydrochloric acid, aqueous sodium carbonate, brine, dried (MgSO$_4$) and evaporated. The residue is subjected to chromatography on silica gel using methanol-ether 1:3 and the eluates are evaporated to give cis-1-acetyl-2-(3,4-dimethoxyphenyl)-3-piperidinol; nmr (CDCl₃) δ 2.12 (s, 3H), 3.86 (s, 6H) and 7.0 (m, 3H).

The latter compound (21.0 g, 75.3 mmoles) in dry tetrahydrofuran (50 ml) is added dropwise to a suspension of lithium aluminum hydride (13.5 g, 350 mmoles) in tetrahydrofuran (150 ml) at 25° C. The mixture is stirred for 30 minutes. Ethyl acetate (50 ml) followed by wet tetrahydrofuran, water and 3N sodium hydroxide are added under nitrogen to the cooled mixture. The mixture is filtered and the filtrate is evaporated to give the title compound, nmr (CDCl₃) δ 0.95 ( , 3H), 1.4–2.9 (m, 10H), 3.2 (m, 2H), 3.75 (m, 1H), 3.9 (s, 6H) and 6.95 (m, 3H).

In the same manner but replacing acetyl chloride with an equivalent amount of cyclopropanecarbonyl chloride butanoyl chloride, cyclohexanecarbonyl chloride, hexanoyl chloride, 3-cyclobutyl-propanoyl chloride, the following compounds of formula II are obtained respectively: (cis-1-cyclopropylmethyl)-2-(3,4-dimethoxyphenyl)-3-piperidinol, nmr (CDCl₃) δ 2.6 (b, 1H), 3.9 (s, 3H) and 7.0 (m, 3H), cis-1-butyl-2-(3,4-dimethoxyphenyl)-3-piperidinol, nmr (CDCl₃) δ 0.82 (m, 3H), 2.4 (b, 1H), 3.88 (s, 6H) and (m, 3H), cis-1-cyclohexylmethyl-2-(3,4-dimethoxyphenyl)-3-piperidinol, cis-1-hexyl-2-(3,4-dimethoxyphenyl)-3-piperidinol, and cis-1-(3-cyclobutylpropyl)-2-(3,4-dimethoxyphenyl)-3-piperidinol.

EXAMPLE 7

[4aα,10bα]-2,3,4,4a,6,10b-Hexahydro-8,9-dimethoxy-1-methyl-6-phenyl-1H-[2]benzopyrano[4,3-b]pyridine; Ia (R¹ = CH₃ and R² = H)

cis-2-(3,4-Dimethoxyphenyl)-1-methyl-3-piperidinol (7.90 g, 31.4 mmoles, described in Example 5) is dissolved in p-dioxane (150 ml) and dry hydrogen chloride is bubbled through the solution until the precipitate has redissolved.

Molecular sieves size 4A beads (5 g) and benzaldehyde (3.1 ml) are added. The hydrogen chloride is bubbled through the stirred solution for an additional 30 minutes. More benzaldehyde (0.3 ml) is added and the mixture is stirred for 30 minutes. The solvent and excess gas are removed under reduced pressure and the residue is dissolved in methylene chloride. The solution is washed with aqueous potassium carbonate, brine, dried (MgSO₄) and evaporated. The residue is subjected to chromatography on alumina (act. 1, basic, Woelm) using ether. The eluates are evaporated to give the title compound. Dry hydrogen bromide is bubbled into a 1:10 ether-methylene chloride solution of the title compound and ether is added. The precipitate is crystallized from acetonitrile-ether to give the title compound as the hydrobromide salt, mp 187°–189° C.

In the same manner but replacing benzaldehyde with an equivalent amount of 3-fluorobenzaldehyde, 4-chlorobenzaldehyde, 2-chlorobenzaldehyde or 3-iodobenzaldehyde, [4aα,10bα]-2,3,4,4a,6,10b-hexahydro-8,9-dimethoxy-1-methyl-6-(3-fluorophenyl)-1H-[2]benzopyrano[4,3-b]pyridine hydrobromide, mp 210°–211° C, [4aα,10bα]-2,3,4,4a,6,10b-hexahydro-8,9-dimethoxy-1-methyl-6-(4-chlorophenyl)-1H-[2]benzopyrano[4,3-b]pyridine, [4aα,10bα]-2,3,4,4a,6,10b-hexahydro-8,9-dimethoxy-1-methyl-6-(2-chlorophenyl)-1H-[2]benzopyrano[4,3-b]pyridine and [4aα,10bα]-2,3,4,4a,6,10b-hexahydro-8,9-dimethoxy-1-methyl-6-(3-iodophenyl)-1H-[2]benzopyrano[4,3-b]pyridine are obtained respectively.

In the sme manner but replacing cis-2-(3,4-dimethoxyphenyl)-1-methyl-3-piperidinol with an equivalent amount of cis-2-(3,4-dimethoxyphenyl)-1-ethyl-3-piperidinol (described in Example 6), cis-1-cyclopropylmethyl-2-(3,4-dimethoxyphenol)-3-piperidinyl (described in Example 6), cis-1-butyl-2-(3,4-dimethoxyphenyl)-3-piperidinol (described in Example 6), cis-1-cyclohexylmethyl-2-(3,4-dimethoxyphenyl)-3-piperidinol (described in Example 6) cis-1-hexyl-2-(3,4-dimethoxyphenyl)-3-piperidinol (described in Example 6) or cis-1-(3-cyclobutylpropyl)-2-(3,4-dimethoxyphenyl)-3-piperidinol and using benzaldehyde, the following compounds of formula I are obtained respectively: [4aα,10bα]-2,3,4,4a,6,10b-hexahydro-1-ethyl-8,9-dimethoxy-6-phenyl-1H-[2]benzopyrano[4,3-b]pyridine hydrobromide, mp > 250° C, [4aα,10bα]-2,3,4,4a,6,10b-hexahydro-1-cyclopropylmethyl-8,9-dimethoxy-6-phenyl-1H-[2]benzopyrano[4,3-b]pyridine hydrobromide, mp 213.5°–214.5° C, [4aα,10bα]-2,3,4,4a,6,10b-hexahydro-1-butyl-8,9-dimethoxy-6-phenyl-1H-[2]benzopyrano-[4,3-b]pyridine hydrobromide, mp 189°–190° C, [4aα,10bα]-2,3,4,4a,6,10b-hexahydro-1-cyclohexylmethyl-8,9-dimethoxy-6-phenyl-1H-[2]benzopyrano[4,3-b pyridine and [4aα,10bα]-2,3,4,4a,6,10b-hexahydro-1-hexyl-8,9-dimethoxy-6-phenyl-1H-[2]benzopyrano[4,3-b]pyridine.

We claim:

1. A compound of formula I

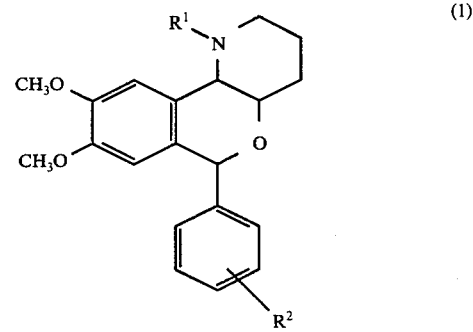

(1)

in which R¹ is lower alkyl or lower cycloalkyl(lower)alkyl and R² is hydrogen or halo, or a therapeutically acceptable acid addition salt thereof.

2. [4aα,10bα]-2,3,4,4a,6,10b-Hexahydro-8,9-dimethoxy-1-methyl-6-phenyl-1H-[2]benzopyrano[4,3-b]pyridine, as claimed in claim 1.

3. [4aα,10bα]-2,3,4,4a,6,10b-Hexahydro-8,9-dimethoxy-1-methyl-6-(3-fluorophenyl)-1H-[2]benzopyrano[4,3-b]pyridine, as claimed in claim 1.

4. [4aα,10bα]-2,3,4,4a,6,10b]-Hexahydro-1-ethyl-8,9-dimethoxy-6-phenyl-1H-[2]-benzopyrano[4,3-b]pyridine, as claimed in claim 1.

5. [4aα,10bα]-2,3,4,4a,6,10b-Hexahydro-1-cyclopropylmethyl-8,9-dimethoxy-6-phenyl-1H-[2]benzopyran[4,3-b]pyridine, as claimed in claim 1.

6. [4aα,10bα]-2,3,4,4a,6,10b-Hexahydro-1-butyl-8,9-dimethoxy-6-phenyl-1H-[2]benzopyrano[4,3-b]pyridine, as claimed in claim 1.

7. The process for preparing a compound of claim 1, comprising:
condensing a compound of formula II

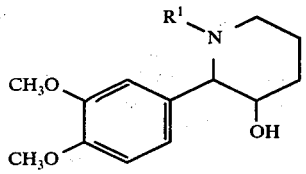

in which $R^1$ is lower alkyl or lower cycloalkyl(lower)alkyl with an aldehyde of formula III

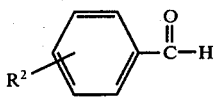

in which $R^2$ is hydrogen or halo in the presence of an acid catalyst to obtain the corresponding compound of formula I in which $R^1$ and $R^2$ are as defined herein.

8. A method for increasing the excretion of urine in a mammal which comprises administering to said mammal an effective diuretic amount of a compound of claim 1, or a therapeutically acceptable salt thereof.

9. A diuretic pharmaceutical composition comprising an effective diuretic amount of compound of claim 1, or a therapeutically acceptable salt thereof, and a pharmaceutically acceptable carrier.

10. A compound of formula Ia

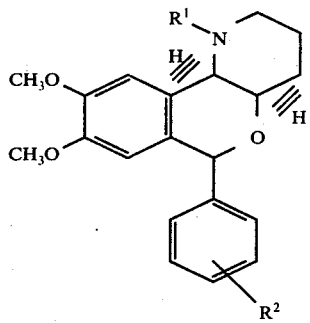

in which $R^1$ is lower alkyl or lower cycloalkyl(lower)alkyl and $R^2$ is hydrogen or halo, or a therapeutically acceptable acid addition salt thereof.

* * * * *